United States Patent
Takahashi et al.

(10) Patent No.: US 6,497,842 B1
(45) Date of Patent: Dec. 24, 2002

(54) QUANTITATIVE CHROMATOGRAPHIC MEASURING DEVICE AND METHOD FOR MANUFACTURING THE SAME

(75) Inventors: Mie Takahashi, Ehime (JP); Masataka Nadaoka, Ehime (JP); Hirotaka Tanaka, Ehime (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/763,368
(22) PCT Filed: Jun. 21, 2000
(86) PCT No.: PCT/JP00/04030
§ 371 (c)(1), (2), (4) Date: Apr. 19, 2001
(87) PCT Pub. No.: WO00/79279
PCT Pub. Date: Dec. 28, 2000

(30) Foreign Application Priority Data

Jun. 21, 1999 (JP) .............................................. 11-174362

(51) Int. Cl.[7] .............................................. B01D 15/08
(52) U.S. Cl. .............................. 422/56; 422/58; 422/70; 210/198.2; 210/198.3; 436/518
(58) Field of Search .............................. 422/56, 58, 70; 436/518; 210/635, 656, 198.2, 198.3

(56) References Cited

U.S. PATENT DOCUMENTS

5,569,608 A    10/1996   Sommer .................... 536/518

FOREIGN PATENT DOCUMENTS

| JP | 05005743 | 1/1993 | ................ 422/56 |
| JP | 8-240591 | 9/1996 | ................ 422/56 |
| JP | 08334511 | 12/1996 | ................ 422/56 |
| JP | 10132820 | 5/1998 | ................ 422/56 |
| JP | 10332700 | 12/1998 | ................ 422/56 |
| JP | 11-94818 | 4/1999 | ................ 422/56 |
| JP | 11094817 | 4/1999 | ................ 422/56 |
| JP | 11094818 | 4/1999 | ................ 422/56 |

*Primary Examiner*—Ernest G. Therkorn
(74) *Attorney, Agent, or Firm*—Wenderoth, Lind & Ponack, L.L.P.

(57) ABSTRACT

In a chromatographic quantitative assay device and a manufacturing method thereof according to the present invention, as shown in FIG. 1, there are provided a non-moistenable reaction layer carrier support 1, a sample addition portion 2 for adding a liquid sample, a marker reagent holding portion 3 for holding a marker reagent, a antibody fixing portion 5 where specific protein is fixed on the region of a reaction layer 4, and a absorption portion 6 for absorbing the liquid sample. These portions are formed above the carrier support 1, and the reaction layer carrier support 1 is covered by close adhesion with the liquid-impermeable sheet member 7 except the portion for adding a liquid sample.

29 Claims, 4 Drawing Sheets

QUANTITATIVE CHROMATOGRAPHIC MEASURING DEVICE AND METHOD FOR MANUFACTURING THE SAME

REFERENCE TO RELATED APPLICATIONS

This application is a 371 of PCT/JP00/04030 filed Jun. 21, 2000.

DESCRIPTION

1. Technical Field

The present invention relates to a chromatographic quantitative assay device for assaying an analyte utilizing antigen-antibody reaction and, more particularly, a chromatographic quantitative assay device including a liquid-impermeable sheet member, and a manufacturing method thereof.

2. Background Art

Conventionally, an assay method by immunochromatography utilizing antigen-antibody reaction is universally taken as an implementation method for chemical or clinical examination of a liquid sample, such as water analysis or urinalysis. Generally, chromatography refers to a method for separating mixtures in accordance with their components, and a specimen used for chromatography comprises a plurality of portions as follows: a portion for adding a liquid sample, a portion for holding a marker reagent which can migrate by infiltration of the liquid sample, a portion that performs binding reaction with the marker reagent containing a substance capable of being bound specifically to a flowing-down analyte, and a portion for absorbing a flowing-down sample. According to this assay method of a chromatographic assay device, chemical reaction which causes coloration or discoloration by color reaction is performed after a predetermined period of time from when the liquid sample was added on the specimen, whereby determination based on visual observation is possible.

Measurement principle by immunochromatography is based on an assay method for identifying antigen or antibody utilizing the specificity of antigen-antibody reaction. The process is as follows: adding a liquid sample to an immunochromatographic specimen, a marker reagent dissolved by the liquid sample extends in infiltration direction and then a substance capable of being bound specifically to an analyte in the liquid sample is fixed, consequently coloration generates in a measurement range. Further, since the result of immunochromatographic analysis is determined by color reaction, it is recorded by the visual observation. In other words, since determination of the result of analysis is extremely easy, the range of use expands.

Such measurement by immunochromatography can be adopted for examinations of various analytes. In some cases with some analytes, however, only semi-quantitative result, at the most, is derived by this method when quantitative result is also required besides qualitative examination. Therefore, advent of any means to lead to more quantitative result of analysis has been desired.

To improve the above-mentioned problems, there is disclosed an immunochromatographic specimen in Japanese Published Patent Application Hei.8-240591. In an assaying method with this immunochromatographic specimen, after a sample was added to this specimen and reaction was done, a coloration degree detected on the specimen is measured as signals of absorption and reflection on the color-reacted portion, by using a detecting instrument. Further, Japanese Published Patent Application Hei.8-334511 discloses a quantitative assay method by immunochromatography using an immunochromatographic specimen, which is performed by taking a coloration degree given by analytic processing of a gradated image of the specimen previously converted after image-capturing by an image sensor.

However, in the case of the quantitative assay method using an immunochromatographic specimen as in the embodiments of the Japanese Published Patent Applications Hei.8-240591 and Hei.8-334511, the quantitative assay method is performed by adopting a suitable detecting instrument in accordance with the degree or level of coloration involved in color reaction. Conventionally, because an immunochromatographic specimen used in general can not be controlled artificially without mechanical control, infiltration rate of liquid sample is dominated by the permeability of the specimen. For example, owing to vaporization of liquid sample from side surfaces of the specimen, the amounts of analyte flowing out toward the measurement range sometimes become heterogeneity. Moreover, in each immunochromatographic specimen used for every measurement, the amount of liquid sample to be added and marker reagent to be added are not always fixed. Accordingly, there is a problem that these causes increase the dispersion of quantitative assay values that appear after a predetermined time.

Additionally, although an assay method by immunochromatography using immunochromatographic specimen is performed after a liquid sample is added and a predetermined period of time has passed, the marker reagent which permeates at this time can begin to dissolve simultaneously, and sometimes remains on the reaction layer as a background. If the value of this background is included in the coloration degree, the detecting instrument executes the measurement including such error. Therefore, quantitative measurement in short time with immunochromatographic specimen is hard to execute. Furthermore, residual amount of the marker reagent flowing out to the reaction layer is inconstant, and is different for every measurement or specimen to use, and thus obtained coloration degree at this time attributed in the error of the reading value greatly.

From the above-mentioned problem, performance of immunochromatographic quantitative assay was extremely close to semi-quantitative due to various standards for specimen and the dispersion of the added liquid sample, or the errors derived from background. Accordingly, the performance improvement of the specimen has been strongly required to enable more accurate measurement.

Further, when carrying out assay of a liquid sample including cell components such as whole blood or bacterial solution, using conventional immunochromatographic specimen, viscosity of the liquid sample and the presence of cell components cause clogging in a reaction layer carrier. Consequently, it takes much time for measurement, and desiccation of the liquid sample during measurement, if any, causes lack of reaction precision and quantitative efficiency. Thereby, simple and easy-handling immunochromatographic quantitative assay device has been strongly required for examination of whole blood, bacterial solution, or the like.

The present invention is made to solve the above-mentioned problems and has for its object to provide an immunochromatographic quantitative assay device and a manufacturing method thereof, which enables precise measurement without influenced by the character of the added liquid sample, accurate reading of coloration degree as a result of reaction of a liquid sample as an analyte and a marker reagent, and results in no influence in the residual amounts of the marker reagent by the background.

SUMMARY OF THE INVENTION

According to a first aspect of the present invention, there is provided a chromatographic quantitative assay device comprising: a non-moistenable reaction layer carrier support and a moistenable layer which is formed above the support and consists of one or arbitrary number of member portions, the moistenable layer comprising a portion for adding a liquid sample, a portion for holding a migratable marker reagent, a portion that performs binding reaction with a marker reagent which is provided with a substance capable of being bound specifically to an analyte in the liquid sample, and a portion for absorbing the liquid sample; and a liquid-impermeable sheet member which is provided being adhered to the upper surface and side surfaces except the portion for adding a liquid sample.

Therefore, in this chromatographic quantitative assay device, it is possible to prevent the vaporization of the moisture, to make the infiltration direction and infiltration state of the liquid sample uniform, and to make the liquid sample and marker reagent, which flow out in a constant time, flow out at uniform concentration.

According to a second aspect of the present invention, there is provided a chromatographic quantitative assay device comprising: a non-moistenable reaction layer carrier support and a moistenable layer which is formed above the support and consists of one or arbitrary number of member portions, the moistenable layer comprising a portion for adding a liquid sample, a portion for holding a constant quantity of migratable combination reagent which is previously prepared consisting of an analyte and a marker reagent, a portion that performs competitive binding reaction between an analyte in the liquid sample and the combination reagent provided with a substance capable of being bound specifically to the analyte in the liquid sample, and a portion for absorbing the liquid sample; and a liquid-impermeable sheet member which is provided being adhered to the upper surface and side surfaces except the portion for adding a liquid sample.

Therefore, in this chromatographic quantitative assay device, it is possible to prevent the vaporization of the moisture, to make the infiltration direction and infiltration state of the liquid sample uniform, and to make the liquid sample and marker reagent, which flow out in a constant time, flow out at uniform concentration.

According to a third aspect of the present invention, there is provided a chromatographic quantitative assay device comprising: a non-moistenable reaction layer carrier support and a moistenable layer which is formed above the support and consists of one or arbitrary number of member portions, the moistenable layer comprising a portion for adding a liquid sample where a substance for destroying cell components in the liquid sample is held, a portion for holding a migratable marker reagent, a portion that performs binding reaction with the marker reagent provided with a substance capable of being bound specifically to an analyte in the liquid sample, and a portion for absorbing the liquid sample; and a liquid-impermeable sheet member which is provided being adhered to the upper surface and side surfaces except the portion for adding a liquid sample.

Therefore, in this chromatographic quantitative assay device, it is possible to prevent the vaporization of the moisture, to make the infiltration state of the liquid sample uniform by destroying cell components in the liquid sample, and to control the quantity of the sample and marker reagent which flow out in a constant time.

According to a fourth aspect of the present invention, there is provided a chromatographic quantitative assay device comprising: a non-moistenable reaction layer carrier support and a moistenable layer which is formed above the support and consists of one or arbitrary number of member portions, the moistenable layer comprising a portion for adding a liquid sample where a substance for destroying cell components in the liquid sample is held, a portion for holding a constant quantity of a migratable combination reagent which is previously prepared consisting of an analyte and a marker reagent, a portion that performs competitive binding reaction between an analyte in the liquid sample and the combination reagent provided with a substance capable of being bound specifically to the analyte in the liquid sample, and a portion for absorbing the liquid sample; and a liquid-impermeable sheet member which is provided being adhered to the upper surface and side surfaces except the portion for adding a liquid sample.

Therefore, in this chromatographic quantitative assay device, it is possible to prevent the vaporization of the moisture, to make the infiltration state of the liquid sample uniform, and to control the quantity of the sample and combination reagent which flow out in a constant time.

According to a fifth aspect of the present invention, in a chromatographic quantitative assay device of any of the first to fourth aspects discussed above, the liquid-impermeable sheet member which is provided being adhered to the upper surface, or from the upper surface to the back surface, except the portion for adding a liquid sample.

Therefore, in this chromatographic quantitative assay device, it is possible to prevent the vaporization of the moisture, and to make the infiltration state of the liquid sample uniform. Furthermore, it is possible to make the marker reagent flow out at uniform concentration, and to restrain the affection of background values added on the values of color-reacted portions.

According to a sixth aspect of the present invention, in a chromatographic quantitative assay device of any of the first to fourth aspects discussed above, the reaction layer carrier support is removed; and the liquid-impermeable sheet member is provided on the periphery except the portion for adding a liquid sample.

Therefore, in this chromatographic quantitative assay device, it is possible to reduce the number of materials. Further, it is possible to make the infiltration state of the liquid sample uniform and to control the quantity of the sample and marker reagent which flow out in a constant time. Moreover, the liquid sample never leaks out of the gap, and the liquid sample never intrudes from the outside except a portion for adding the sample.

According to a seventh aspect of the present invention, in a chromatographic quantitative assay device of any of the first to fourth aspects discussed above, the vertical side surfaces of the liquid-impermeable sheet member is opened in the direction where the liquid sample infiltrates.

Therefore, in this chromatographic quantitative assay device, the air-releasing path at infiltration of liquid is restricted in only the infiltration direction, whereby it is possible that liquid sample and marker reagent flow out at uniform concentration.

According to an eighth aspect of the present invention, in a chromatographic quantitative assay device of any of the first to fourth aspects discussed above, the end of the liquid-impermeable sheet member is opened at an arbitrary position at the end of the chromatographic quantitative assay device in the direction where the liquid sample infiltrates.

Therefore, in this chromatographic quantitative assay device, the air-releasing path at infiltration of liquid is restricted in only the infiltration direction, whereby it is possible that liquid sample and marker reagent flow out at uniform concentration.

According to a ninth aspect of the present invention, in a chromatographic quantitative assay device of any of the first to fourth aspects discussed above, the liquid-impermeable sheet member is adhered by an adhesive made of an arbitrary adhesive.

Therefore, in this chromatographic quantitative assay device, it is possible to prevent the vaporization of the moisture, to make the infiltration direction and infiltration state of the liquid sample uniform, and to make the liquid sample and marker reagent, which flow out in a constant time, flow out at uniform concentration, as well as to prevent the liquid-impermeable sheet member from exfoliation by infiltration of the liquid sample.

According to a tenth aspect of the present invention, in a chromatographic quantitative assay device of any of the first to fourth aspects discussed above, the liquid-impermeable sheet member is adhered by an arbitrary adhesive which hardens after adhesion.

Therefore, in this chromatographic quantitative assay device, it is possible to prevent the vaporization of the moisture, to make the infiltration direction and infiltration state of the liquid sample uniform, and to make the liquid sample and marker reagent, which flow out in a constant time, flow out at uniform concentration, as well as, to prevent the liquid-impermeable sheet member from exfoliation by infiltration of the liquid sample. Further, because the adhesive is hardened after adhesion, it is possible to prevent attachment of the paste to a cutter when the sensor is cut. Moreover, it is possible to facilitate mass production, as well as, to prevent transition of paste to reaction layer, thereby preventing transformation of reaction layer carrier or specific protein, whereby the performance of the chromatographic quantitative assay device can be maintained over a long period.

According to an eleventh aspect of the present invention, in a chromatographic quantitative assay device of the ninth aspect discussed above, the adhesive applied to the liquid-impermeable sheet member is made of thermoplastic resin.

Therefore, in this chromatographic quantitative assay device, it is possible to prevent the vaporization of the water, to make the infiltration direction and infiltration state of the liquid sample uniform, and to make the liquid sample and marker reagent, which flow out in a constant time, flow out at uniform concentration, as well as, to prevent the liquid-impermeable sheet member from exfoliation by infiltration of the liquid sample. Further, because the adhesive is hardened by cooling after adhesion, it is possible to prevent attachment of the paste to a cutter when the sensor is cut. Moreover, it is possible to facilitate mass production, as well as, to prevent transition of paste to reaction layer, thereby preventing transformation of reaction layer carrier or specific protein, whereby the performance of the chromatographic quantitative assay device can be maintained over a long period.

Here, the thermoplastic resin is a resin having the property that it is in a solid state at normal temperature, softens when heated to be processed, and solidifies when cooled thereafter. That is, it has the property that the plasticity is held reversibly by repetition of cooling and heating. The thermoplastic resin of this kind includes polyethylene, polypropylene, polychlorinated vinyl, polystyrene, polychlorinated vinylidene, fluororesin, methyl polymethacrylate, polyamide, polyester, polycarbonate, polyphenylene oxide, polyurethane, polyacetal, or the like.

According to a twelfth aspect of the present invention, in a chromatographic quantitative assay device of the ninth aspect discussed above, the adhesive applied to the liquid-impermeable sheet member is made of thermosetting resin.

Therefore, in this chromatographic quantitative assay device, it is possible to prevent vaporization of the moisture, to make the infiltration direction and infiltration state of the liquid sample uniform, and to make the liquid sample and marker reagent, which flow out in a constant time, flow out at uniform concentration, as well as, to prevent the liquid-impermeable sheet member from exfoliation by infiltration of the liquid sample. Further, because the adhesive is hardened after adhesion and is not melted, it is possible to prevent attachment of the paste to a cutter when the sensor is cut. Moreover, it is possible to facilitate mass production, as well as, to prevent transition of paste to reaction layer, thereby preventing transformation of reaction layer carrier or specific protein, whereby the performance of a chromatographic quantitative assay device can be maintained over a long period.

Here, the thermosetting resin is a resin having the property that it softens when heated to be processed, but hardens by further heating and thus does not soften thereafter. The thermosetting resin of this kind includes urea resin, melamine resin, phenol resin, or the like.

According to a thirteenth aspect of the present invention, in a chromatographic quantitative assay device of any of the first to fourth aspects discussed above, the liquid-impermeable sheet member is made of an arbitrary transparent or semi-transparent liquid-impermeable material.

Therefore, in this chromatographic quantitative assay device, it is possible to prevent the vaporization of the moisture, to make the infiltration direction and infiltration state of the liquid sample uniform, and to make the liquid sample and marker reagent, which flow out in a constant time, flow out at uniform concentration, as well as, to enable visual detection when measuring the results on the detection region from the outside, whereby it is easy to perform the measurement.

According to fourteenth aspect of the present invention, a chromatographic quantitative assay device of any of the first to fourth aspects discussed above, the liquid-impermeable sheet member is made of an arbitrary semi-transparent or opaque liquid-impermeable material, and a transparent window is provided at the detection region.

Therefore, in this chromatographic quantitative assay device, it is possible to prevent the vaporization of the moisture, to make the infiltration direction and infiltration state of the liquid sample uniform, and to make the liquid sample and marker reagent, which flow out in a constant time, flow out at uniform concentration, as well as, to enable visual detection when measuring the results on the detection region from the outside, whereby it is easy to perform the measurement.

According to a fifteenth aspect of the present invention, in a chromatographic quantitative assay device of the third or fourth aspects discussed above, the substance for destroying cell components held at the portion for adding a liquid sample is a surfactant.

Therefore, in this chromatographic quantitative assay device, it is possible to prevent the vaporization of the moisture, to make the infiltration direction and infiltration state of the liquid sample uniform, and to make the liquid sample and marker reagent, which flow out in a constant time, flow out at uniform concentration, as well as, to avoid clogging to be caused by cell components in a liquid sample such as whole blood or bacterial solution, thereby to make the infiltration state uniform, resulting in more precise quantitative measurement in a short time.

According to a sixteenth aspect of the present invention, in a chromatographic quantitative assay device of the third or fourth aspects discussed above, the substance for destroying cell components held at the portion for adding a liquid sample is composed of chloride such as sodium chloride, potassium chloride.

Therefore, in this chromatographic quantitative assay device, it is possible to prevent the vaporization of the moisture, to make the infiltration direction and infiltration state of the liquid sample uniform, and to make the liquid sample and marker reagent, which flow out in a constant time, flow out at uniform concentration, as well as, to avoid clogging to be caused by cell components in a liquid sample such as whole blood or bacterial solution, thereby to make the infiltration state uniform, resulting in more precise quantitative measurement in a short time without inhibition of binding reaction.

According to a seventeenth aspect of the present invention, in a chromatographic quantitative assay device of the third or fourth aspect discussed above, the substance for destroying cell components held at the portion for adding a liquid sample is saponin series.

Therefore, in this chromatographic quantitative assay device, it is possible to prevent the vaporization of the moisture, to make the infiltration direction and infiltration state of the liquid sample uniform, and to make the liquid sample and marker reagent, which flow out in a constant time, flow out at uniform concentration, as well as, to avoid clogging to be caused by cell components in a liquid sample such as whole blood or bacterial solution, thereby to make the infiltration state uniform, resulting in more precise quantitative measurement in a short time.

According to an eighteenth aspect of the present invention, in a chromatographic quantitative assay device of the third or fourth aspects discussed above, the substance for destroying cell components held at the portion for adding a liquid sample is a substance having bacteriolytic effect such as lysozyme.

Therefore, in this chromatographic quantitative assay device, it is possible to prevent the vaporization of the moisture, to make the infiltration direction and infiltration state of the liquid sample uniform, and to make the liquid sample and marker reagent, which flow out in a constant time, flow out at uniform concentration, as well as, to avoid clogging to be caused by cell components in a liquid sample such as bacterial solution or thereby to make the infiltration state uniform, resulting in more precise quantitative measurement in a short time without inhibition of binding reaction.

According to a nineteenth aspect of the present invention, a manufacturing method of a chromatographic quantitative assay device of any of the first to fourth aspects discussed above, the liquid-impermeable sheet member, which is previously treated by performing aging at an arbitrary temperature, is adhered closely to the upper surface and side surfaces of the chromatographic quantitative assay device.

Therefore, in this chromatographic quantitative assay device, it is possible to prevent the vaporization of the moisture, to make the infiltration direction and infiltration state of the liquid sample uniform, and to make the liquid sample and marker reagent, which flow out in a constant time, flow out at uniform concentration, as well as, to accelerate the volatilization of organic solvent which brings adverse effects on the protein contained in the adhesive for the liquid-impermeable sheet member or on the reaction layer by performing aging, whereby preservation stability over a longer period is realized.

Here, the aging means leaving the liquid-impermeable sheet member for an arbitrary period of time under arbitrary and constant environment.

According to a twentieth aspect of the present invention, a manufacturing method of a chromatographic quantitative assay device of any of the first to fourth aspects discussed above, the liquid-impermeable sheet member is adhered closely to the upper surface and side surfaces of the chromatographic quantitative assay device by applying of an arbitrary pressure to the liquid-impermeable sheet member at an arbitrary temperature.

Therefore, in this chromatographic quantitative assay device, it is possible to prevent the vaporization of the moisture, to make the infiltration direction and infiltration state of the liquid sample uniform, and to make the liquid sample and marker reagent, which flow out in a constant time, flow out at uniform concentration, as well as, to adhere the liquid-impermeable sheet member onto the front surface and the side surfaces of the chromatographic quantitative assay device more solidly.

Here, the liquid-impermeable sheet member means e.g. an adhesive sheet material of heat seal type, therefore adhesion of a sheet material by laminating processing as seen in thermocompression bonding or the like is enabled.

According to a twenty-first aspect of the present invention, in a manufacturing method of a chromatographic quantitative assay device of the nineteenth or twentieth aspects discussed above, the adhesive applied to the liquid-impermeable sheet member has a characteristic of being melted and taking on stickiness at the temperature higher than normal temperatures and is hardened after adhesion.

Therefore, in this chromatographic quantitative assay device, it is possible to prevent the vaporization of the moisture, to make the infiltration direction and infiltration state of the liquid sample uniform, and to make the liquid sample and marker reagent, which flow out in a constant time, flow out at uniform concentration, as well as, to prevent the liquid-impermeable sheet member from exfoliation by infiltration of the liquid sample. Further, because the adhesive is hardened after adhesion, it is possible to prevent attachment of the paste to a cutter when the sensor is cut. Moreover, it is possible to facilitate mass production, as well as, to prevent transition of paste to reaction layer, thereby preventing transformation of reaction layer carrier or specific protein, whereby a manufacturing method of specimen that can keep the performance of the chromatographic quantitative assay device over a long period is provided.

Here, the adhesive is an adhesive having the property that it softens when heated and hardens when cooled after adhesion and, preferably, an adhesive having a low melting point as not to soften at normal temperature and to melt at lower temperature.

According to a twenty-second aspect of the present invention, a manufacturing method of a chromatographic quantitative assay device of the twenty-first aspect discussed above, the adhesive applied to the liquid-impermeable sheet member is made of thermoplastic resin.

Therefore, in this chromatographic quantitative assay device, it is possible to prevent the vaporization of the moisture, to make the infiltration direction and infiltration state of the liquid sample uniform, and to make the liquid sample and marker reagent, which flow out in a constant time, flow out at uniform concentration, as well as, to prevent the liquid-impermeable sheet member from exfoliation by infiltration of the liquid sample. Further, because the adhesive is hardened by cooling after adhesion, it is possible to prevent attachment of the paste to a cutter when the sensor is cut. Moreover, it is possible to facilitate mass production, as well as, to prevent transition of paste to reaction layer, thereby preventing transformation of reaction layer carrier or specific protein, whereby the performance of the chromatographic quantitative assay device can be maintained over a long period.

According to a twenty-third aspect of the present invention, a manufacturing method of a chromatographic quantitative assay device of the twenty-first aspect discussed above, the adhesive applied to the liquid-impermeable sheet member is made of thermosetting resin.

Therefore, in this chromatographic quantitative assay device, it is possible to prevent the vaporization of the moisture, to make the infiltration direction and infiltration state of the liquid sample uniform, and to make the liquid sample and marker reagent, which flow out in a constant time, flow out at uniform concentration, as well as, to prevent the liquid-impermeable sheet member from exfoliation by infiltration of the liquid sample. Further, because the adhesive is hardened after adhesion and is not melted, it is possible to prevent attachment of the paste to a cutter when the sensor is cut. Moreover, it is possible to facilitate mass production, as well as, to prevent transition of paste to reaction layer, thereby preventing transformation of reaction layer carrier or specific protein, whereby the performance of a chromatographic quantitative assay device can be maintained over a long period.

BEST MODE TO EXECUTE THE INVENTION

Embodiment 1

Hereinafter, embodiment 1 of the present invention mentioned in claim 1 will be described with reference to FIGS. 1 and 2.

Figure 1:
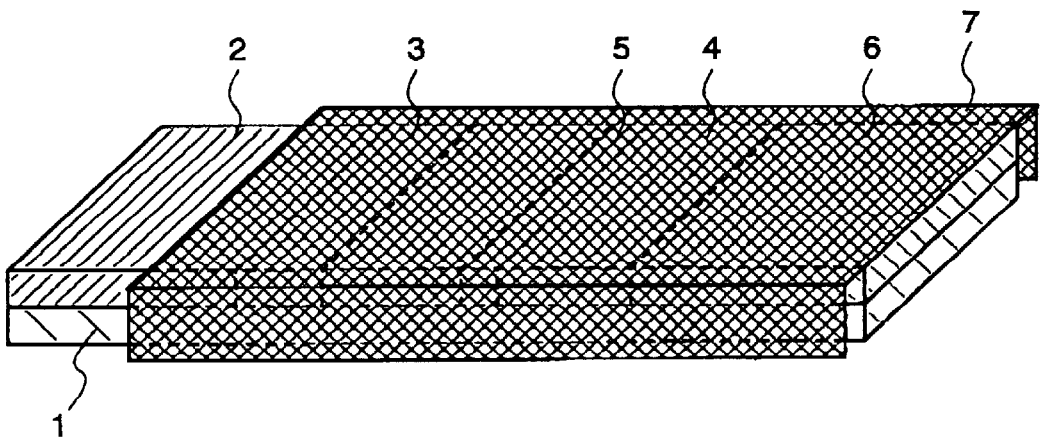
FIG. 1 is a block diagram illustrating a chromatographic quantitative assay device in embodiments of the present invention.
Figure 2:
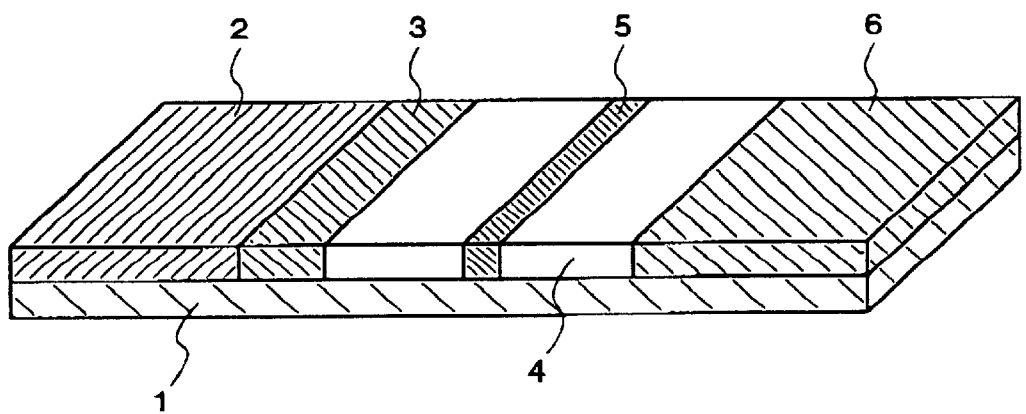
FIG. 2 is an immunochromatographic specimen for a chromatographic quantitative assay device, wherein liquid-impermeable sheet member is removed, in embodiments of the present invention.

FIG. 1 is a block diagram illustrating a chromatographic quantitative assay device in an embodiment of the present invention, and FIG. 2 shows an immunochromatographic specimen obtained by removing a liquid-impermeable sheet member from the chromatographic quantitative assay device shown in FIG. 1.

In FIG. 2, the reference numerals designate respective portions: 1 is a reaction layer carrier support composed of plastic or the like for supporting chromatographic materials, 2 is a sample addition portion made of an absorbent material such as non-woven fabric for adding or applying a liquid sample, 3 is a marker reagent holding portion for holding a marker reagent so as to dissolve into the non-woven fabric or the like, 4 is a reaction layer composed of nitrocellulose or the like, 5 is an antibody fixing portion for fixing specific protein on the region of the reaction layer 4, 6 is an absorption portion by which the liquid sample is finally absorbed. The portions 2 to 6 are respectively formed above the reaction layer carrier support 1. Further, in FIG. 1, the reference numeral 7 designates a liquid-impermeable sheet member composed of plastic tape or the like, with which the upper surface of the specimen in FIG. 2 is covered.

An assay method of the chromatographic quantitative assay device will be described.

At the start of assaying, because a part of the sample addition portion 2 is not covered with the liquid-impermeable sheet member 7, the liquid sample is added to the non-covered part. The liquid sample which is added on the sample addition portion 2 reaches the region of the marker reagent holding portion 3, and the marker reagent held in the region of the marker reagent holding portion 3 is dissolved by infiltration of the liquid sample and then infiltrates to the region of the reaction layer 4. There is provided an antibody fixing portion 5 in which specific protein is mixed, on the region of the reaction layer 4, and this portion 5 performs binding reaction with the marker reagent dissolved out from the marker reagent holding portion 3. At this point in time, if the analyte is present in the liquid sample, any color reaction is observed at the region of the antibody fixing portion 5. At the last, the liquid sample is absorbed at the absorption portion 6, and the reaction is finished. By measuring the color reaction which appears at the antibody fixing portion 5 using an arbitrary detecting instrument, quantitative assay can be carried out.

Here, the number of region of the antibody fixing portion 5 may not necessarily be one, arbitrary number of region of specific protein can exist on the region of the reaction layer 4. Further, while plastic or the like is taken herein as a material of the reaction layer carrier support 1, other arbitrary liquid-impermeable sheet materials can also be adopted. Moreover, non-woven fabric and nitrocellulose, which are taken herein as materials of the sample addition portion 2, the marker reagent holding portion 3, the reaction layer 4 and the absorption portion 6, are merely examples, and thus, other arbitrary porous carriers can also be adopted.

Thus, according to the chromatographic quantitative assay device of embodiment 1, because the upper surface and side surfaces of the chromatographic quantitative assay device are covered with close adhesion with the liquid-impermeable sheet member 7 except a part for adding the liquid sample, it is possible to prevent vaporization of the water and to make infiltration state of the liquid sample uniform. In other words, it is possible to make the liquid sample and marker reagent, which flow out in a constant time, flow out at uniform concentration. In the conventional method, because the marker reagent with high concentration flows out at once due to the centralization of the marker reagent at a pointed end of the liquid sample, there remains some of the marker reagent which does not react. On the other hand, in embodiment 1 of the present invention, because the residual amount of the marker reagent which does not react is restrained, it is possible to reduce the affection of background values as a cause of measurement error due to the residual marker reagent. Therefore, because the affection of background values added on the color-reacted portions is reduced, it is possible to perform the assay in short time, whereby a chromatographic quantitative assay device with higher sensitivity and higher performance can be obtained.

Embodiment 2

Hereinafter, embodiment 2 of the present invention mentioned in claim 2 will be described with reference to FIGS. 1 and 2 described in embodiment 1.

In FIG. 2, reference numeral 3 designate a marker combination reagent holding portion in which a previously-prepared combination reagent composed of an analyte and a marker reagent is held by a predetermined quantity so as to dissolve into non-woven fabric or the like. Here, regarding to the reference numerals to be referred to in FIGS. 1 and 2, same reference numerals designate the same or corresponding parts described in embodiment 1.

An assay method of the chromatographic quantitative assay device will be described.

At the start of assaying, because a part of the sample addition portion 2 is not covered with the liquid-impermeable sheet member 7, the liquid sample is added to the non-covered part. The liquid sample added on the sample addition portion 2 reaches the region of the marker combination reagent holding portion 3, and an analyte and a combination reagent held in the region of the marker combination reagent holding portion 3 are dissolved by infiltration of the liquid sample and then infiltrates to a region of the reaction layer 4. There is provided an antibody fixing portion 5 in which specific protein is fixed, on the region of the reaction layer 4, and this portion 5 performs competitive binding reaction between the combination reagent dissolved out from the region of the marker combination reagent holding portion 3 and the analyte in the liquid sample. At this point in time, if the analyte is not present in the liquid sample, color reaction is observed at the region of the antibody fixing portion 5. Contrarily, if the analyte is present in the liquid sample, color reaction in proportion to the concentration of the analyte in the liquid sample is observed at the region of the antibody fixing portion 5. At the last, the liquid sample is absorbed at the absorption portion 6, and the reaction is finished. By measuring the color reaction which appears at the antibody fixing portion 5 using an arbitrary detecting instrument, quantitative assay can be carried out.

Here, the number of region of the antibody fixing portion 5 may not necessarily be one, arbitrary number of region of specific protein can exist on the region of the reaction layer 4. Further, while plastic or the like is taken herein as a material of the reaction layer carrier support 1, other arbitrary liquid-impermeable sheet materials can also be adopted. Moreover, non-woven fabric and nitrocellulose, which are taken herein as materials of the sample addition portion 2, the marker combination reagent holding portion 3, the reaction layer 4 and the absorption portion 6, are merely examples, and thus, other arbitrary porous carriers can also be adopted.

Thus, according to the chromatographic quantitative assay device of embodiment 2, the upper surface and side surfaces of the chromatographic quantitative assay device are covered by close adhesion with the liquid-impermeable sheet member 7 except a part for adding the liquid sample, and therefore, it is possible to prevent vaporization of the water and to make infiltration state of the liquid sample uniform. In other words, it is possible to make the liquid sample and marker combination reagent, which flow out in a constant time, flow out at uniform concentration. In the conventional method, because the marker combination reagent with high concentration flows out at once due to centralization of the marker combination reagent at a pointed end of the liquid sample, there remains some of the marker combination reagent which does not react. On the other hand, in embodiment 2 of the present invention, because the residual quantity of the combination reagent which does not react is restrained, it is possible to reduce the affection of background values and blank values as a cause of measurement error due to the residual combination reagent. Therefore, the affection of the background values and blank values added on the color-reacted portions can also be reduced, whereby it is possible to perform the assay in short time, resulting in a competitive chromatographic quantitative assay device with high sensitivity and higher performance.

Embodiment 3

Hereinafter, embodiment 3 of the present invention mentioned in claim 3 will be described with reference to FIGS. 1 and 2 described in embodiment 1.

In FIG. 2, reference numeral 2 designates a sample addition portion made of an absorbent material such as non-woven fabric for holding a cell component destruction substance. Reference numeral 3 designates a marker reagent holding portion in which a marker reagent is held so as to dissolve into the non-woven fabric or the like. Here, regarding to the reference numerals to be referred to in FIGS. 1 and 2, same reference numerals designate the same or corresponding parts described in embodiment 1.

An assay method of the chromatographic quantitative assay device will be described.

At the start of assaying, because a part of the sample addition portion 2 is not covered with the liquid-impermeable sheet member 7, the liquid sample is added to the non-covered part. After the liquid sample is added on the sample addition portion 2, cell components in the liquid sample are destroyed by the actuation of cell component destruction substance contained in the liquid sample. The liquid sample, which contains such destroyed cell components, reaches the region of the marker reagent holding portion 3, and the marker reagent held in the region of the marker reagent holding portion 3 is dissolved by infiltration of the liquid sample and then infiltrates to the region of the reaction layer 4. There is provided an antibody fixing portion 5 in which specific protein is fixed, on the region of the reaction layer 4, and this portion 56 performs binding reaction with the marker reagent dissolved out from the region of the marker reagent holding portion 3. At this point in time, if the analyte is present in the liquid sample, any color reaction is observed at the region of the antibody fixing portion 5. At the last, the liquid sample is absorbed at the absorption portion 6, and the reaction is finished. By measuring the color reaction which appears at the antibody fixing portion 5 using an arbitrary detecting instrument, quantitative assay can be carried out.

Here, the number of region of the antibody fixing portion 5 may not necessarily be one, arbitrary number of region of specific protein can exist on the region of the reaction layer 4. Further, while plastic or the like is taken herein as a material of the reaction layer carrier support 1, other arbitrary liquid-impermeable sheet materials can also be adopted. Moreover, non-woven fabric and nitrocellulose, which are taken herein as materials of the sample addition portion 2, the marker reagent holding portion 3, the reaction layer 4 and the absorption portion 6, are merely examples, and thus other arbitrary porous carriers can also be adopted.

Thus, according to the chromatographic quantitative assay device of embodiment 3, since the sample addition portion is provided with a part for holding a cell component destruction substance, the cell components in the liquid sample are destroyed by this substance, whereby infiltration on the reaction layer carrier is smoothly performed. Further, because the upper surface and side surfaces of the chromatographic quantitative assay device are covered by close adhesion with the liquid-impermeable sheet member 7 except a part that the liquid sample is added, it is possible to prevent vaporization of the water and to make infiltration state of the liquid sample uniform. In other words, it is possible to make the liquid sample and marker reagent, which flow out in a constant time, flow out at uniform concentration. In the conventional method, cell components in the liquid sample make the viscosity of the liquid sample higher, and then clogging occurs in the process of infiltration into the reaction layer carrier, and thereby, infiltration rate is remarkably lowered. Further, because the marker reagent with high concentration flows out at once due to centralization of the marker reagent at a pointed end of the liquid sample, there remains some of the marker reagent which does not react. On the other hand, in embodiment 3 of the present invention, because cell components in the liquid sample are destroyed, it is possible to prevent the reaction layer carrier from clogging and to keep infiltration rate in the constant. Further, it is possible to restrain residual amount of the marker reagent which does not react, and thereby the affection of background values as a cause of measurement error due to residual marker reagent can be reduced. Since the clogging by cell components is prevented and the affection of background values added on the values of color-reacted portions is reduced, it is possible to perform the assay in short time when the liquid sample containing cell components is adopted, whereby a chromatographic quantitative assay device with higher sensitivity and higher performance can be obtained.

Embodiment 4

Hereinafter, embodiment 4 of the present invention mentioned in claim 4 will be described with reference to FIGS. 1 and 2 described in embodiment 1.

In FIG. 2, reference numeral 2 designate a sample addition portion made of an absorbent material such as non-woven fabric for adding or applying a liquid sample, in which a cell component destruction substance is held. Reference numeral 3 designate a marker combination reagent holding portion in which a previously-prepared combination reagent composed of an analyte and a marker reagent is held by a predetermined quantity so as to dissolve into non-woven fabric or the like. Here, regarding to the reference numerals to be referred to in FIGS. 1 and 2, same reference numerals designate the same or corresponding parts described in embodiment 1.

An assay method of the chromatographic quantitative assay device will be described.

At the start of assaying, because a part of the sample addition portion 2 is not covered with the liquid-impermeable sheet member 7, the liquid sample is added to the non-covered part. After the liquid sample is added on the sample addition portion 2, cell components in the liquid sample are destroyed by the actuation of cell component destruction substance contained in the liquid sample. The liquid sample containing such destroyed cell components reaches the region of the marker combination reagent holding portion 3, and an analyte and a combination reagent held in the region of the marker combination reagent holding portion 3 are dissolved by infiltration of the liquid sample, and then infiltrates to the region of the reaction layer 4. There is provided an antibody fixing portion 5 in which specific protein is fixed, on the region of the reaction layer 4. In this portion, competitive binding reaction is performed between the combination reagent dissolved out from the region of the marker combination reagent holding portion 3 and the analyte in the liquid sample. At this point in time, if the analyte is not present in the liquid sample, color reaction is observed at the region of the antibody fixing portion 5. Contrarily, if the analyte is present in the liquid sample, color reaction in proportion to the concentration of the analyte in the liquid sample is observed at the region of the antibody fixing portion 5. At the last, the liquid sample is absorbed at the absorption portion 6, and the reaction is finished. By measuring the color reaction which appears at the antibody fixing portion 5 using an arbitrary detecting instrument, quantitative assay is carried out.

Here, the number of region of the antibody fixing portion 5 may not necessarily be one, arbitrary number of region of specific protein can exist on the region of the reaction layer 4. Further, while plastic or the like is taken herein as a material of the reaction layer carrier support 1, other arbitrary liquid-impermeable sheet materials can also be adopted. Moreover, non-woven fabric and nitrocellulose, which are taken herein as materials of the sample addition portion 2, the marker combination reagent holding portion 3, the reaction layer 4 and the absorption portion 6, are merely examples, and thus, other arbitrary porous carriers can also be adopted.

Thus, the chromatographic quantitative assay device of embodiment 4 is provided with a part for holding a cell component destruction substance, cell components in the liquid sample are destroyed by this substance, whereby infiltration on the reaction layer carrier is smoothly performed. Further, the upper surface and side surfaces of the chromatographic quantitative assay device are covered with the liquid-impermeable sheet member 7 except a part that the liquid sample is added, and therefore, it is possible to prevent vaporization of the water and to make infiltration state of the liquid sample uniform. In other words, it is possible to make the liquid sample and marker reagent, which flow out in a constant time, flow out at uniform concentration. In the conventional method, cell components in the liquid sample make the viscosity of the liquid sample higher, and then clogging occurs in the process of infiltration into the reaction layer carrier, and thereby, infiltration rate is remarkably lowered. Further, because the marker reagent with high concentration flows out at once due to the centralization of the marker reagent at a pointed end of the liquid sample, there remains some of the marker reagent which does not react. On the other hand, in embodiment 4 of the present invention, because cell components in the liquid sample are destroyed, it is possible to prevent the reaction layer carrier from clogging and to keep infiltration rate in the constant. Furthermore, it is possible to restrain residual amount of the marker reagent which does not react, and thereby the affection of background values as a cause of measurement error due to the residual marker reagent can be reduced. Since the clogging by cell components is prevented and the affection of background values added on the values of color-reacted portions is reduced, it is possible to perform the assay in short time when the liquid sample containing cell components is adopted, resulting in a chromatographic quantitative assay device with higher sensitivity and higher performance.

Embodiment 5

Hereinafter, embodiment 5 of the present invention mentioned in claim 5 will be described with reference to FIGS. 3 and 4.

Figure 3:
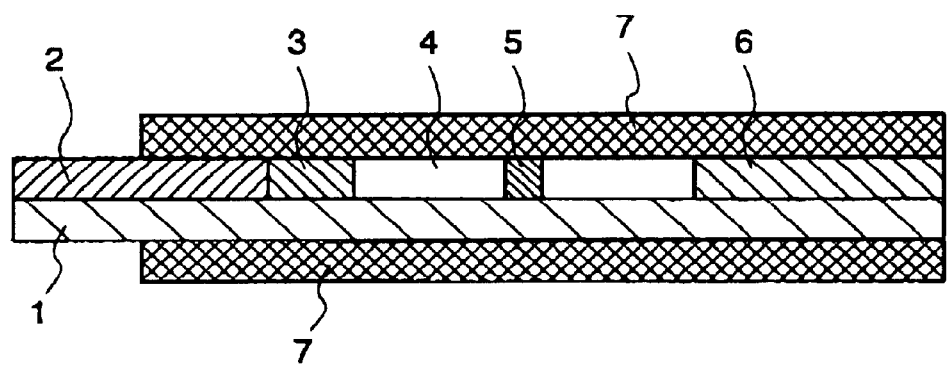
FIG. 3 is a block diagram illustrating a chromatographic quantitative assay device in embodiment 5 of the present invention.
Figure 4:
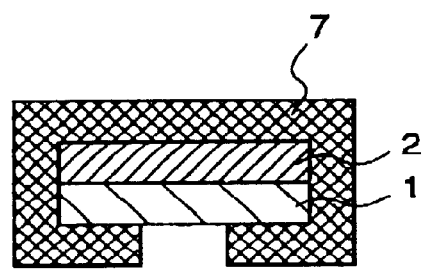
FIG. 4 is a partial view, at the side surfaces in vertical to the infiltration direction, of a chromatographic quantitative assay device in embodiment 5 of the present invention.

FIG. 3 is a block diagram illustrating a chromatographic quantitative assay device according to embodiment 5 of the present invention, an FIG. 4 is a partial view, at the side surfaces in vertical to the infiltration direction of a chromatographic quantitative assay device in FIG. 3. In FIG. 4, while it is seen that the sample addition portion 2 is provided between the reaction layer carrier support 1 and the liquid-impermeable sheet member 7, there is provided the absorption portion 6 on the opposite vertical side surfaces at the same position of the sample addition portion 2.

In FIGS. 3 and 4, the liquid-impermeable sheet member 7 covers the upper surface, parallel side surfaces and the back surface of the reaction layer carrier so as to be adhered closely in the direction where the liquid sample infiltrates. Since a part of the sample addition portion 2 of this chromatographic quantitative assay device is not covered with the liquid-impermeable sheet member 7, a liquid sample is added on the non-covered part, and the assay is performed. Here, regarding to the reference numerals to be referred to in FIGS. 3 and 4, same reference numerals designate the same or corresponding parts described in embodiment 1.

Thus, according to the chromatographic quantitative assay device of embodiment 5, because the liquid-impermeable sheet member 7 covers, by close adhesion, the upper surface or from the upper surface to the back surface of the chromatographic quantitative assay device except a part that the liquid sample is added, it is possible to prevent vaporization of the water and to make infiltration state of the liquid sample uniform. In other words, it is possible to make the liquid sample and marker regent, which flow out in a constant time, flow out at uniform concentration. Further, because the affection of background values added to the color-reacted portions is reduced, it is possible to perform the assay in short time, whereby a chromatographic quantitative assay device with higher sensitivity and higher performance can be obtained. Moreover, the liquid sample never leaks out of the gap, and the liquid sample never intrudes from the outside except the sample addition portion 2.

Embodiment 6

Hereinafter, embodiment 6 of the present invention mentioned in claim 6 will be described with reference to FIGS. 5 and 6.

Figure 5:
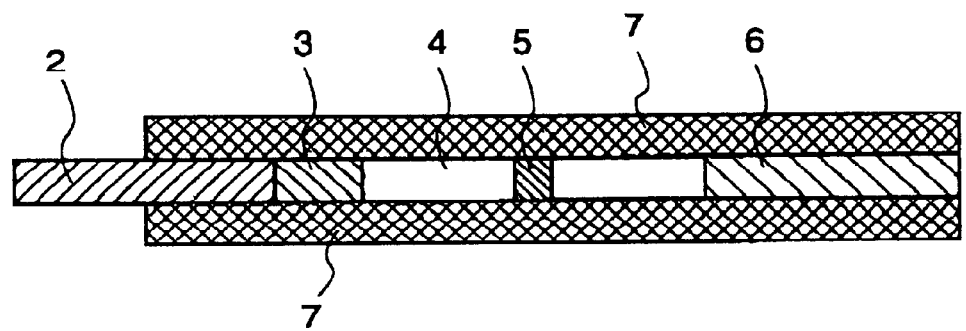
FIG. 5 is a block diagram illustrating that a liquid-impermeable sheet member serves as also a reaction layer carrier support in a chromatographic quantitative assay device in embodiment 6 of the present invention.
Figure 6:
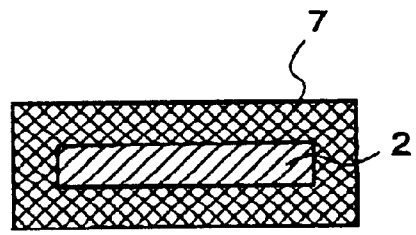
FIG. 6 is a partial view, at the side surfaces in vertical to the infiltration direction, of a chromatographic quantitative assay device in embodiment 6 of the present invention.

FIG. 5 is a block diagram illustrating a chromatographic quantitative assay device according to embodiment 6 of the present invention, and FIG. 6 is a partial view, at the side surfaces in vertical to the infiltration direction, of a chromatographic quantitative assay device shown in FIG. 5. In FIG. 6, while it is seen that the sample addition portion 2 is provided between the liquid-impermeable sheet members 7, there is provided an absorption portion 6 on the opposite vertical side surfaces at the same position of the sample addition portion 2.

In FIGS. 5 and 6, the chromatographic quantitative assay device is configured such that the reaction layer carrier support 1 (see FIG. 1) is removed, and that the periphery of a reaction layer carrier is covered with the liquid-impermeable sheet member 7 so as to be adhered closely in the direction where the liquid sample infiltrates. In other words, the liquid-impermeable sheet member 7 is constituted to also serve as a reaction layer carrier support 1. Since a part of the sample addition portion 2 of this chromatographic quantitative assay device is not covered with the liquid-impermeable sheet member 7, a liquid sample is added from the non-covered part, and the assay is performed. Here, regarding to the reference numerals to be referred to in FIGS. 5 and 6, same reference numerals designate the same or corresponding parts mentioned in embodiment 1.

Thus, according to the chromatographic quantitative assay device of embodiment 6, since the liquid-impermeable sheet member 7 serves also as a reaction layer carrier support, it is possible to reduce the number of materials of the chromatographic assay device. Further, since the periphery of the chromatographic quantitative assay device is covered with the liquid-impermeable sheet member 7 being adhered closely, vaporization of the water is prevented, and the air-releasing path at infiltration of liquid is restricted only in the infiltration direction so as to make the infiltration of the liquid sample uniform, whereby it is possible to make the liquid sample and marker reagent, which flow in a constant time, flow out at uniform concentration. Moreover, since the affection of background values added on the color-reacted portions can be reduced, it is possible to perform the assay in short time, resulting in a chromatographic quantitative assay device with higher sensitivity and higher performance. Moreover, liquid sample never leaks out of the gap, and liquid sample never intrudes from the outside except the sample addition portion 2.

Embodiment 7

Hereinafter, embodiment 7 of the present invention mentioned in claims 7 and 8 will be described with reference to FIG. 1 mentioned in embodiment 1.

FIG. 1 is a block diagram illustrating a chromatographic quantitative assay device according to embodiment 7 of the present invention. Here, regarding to the reference numerals to be referred to in FIG. 1, same reference numerals designate the same or corresponding parts mentioned in embodiment 1.

In FIG. 1, the liquid-impermeable sheet member is opened at an arbitrary position of the vertical side surfaces or the end of the chromatographic quantitative assay device in the direction where the liquid sample infiltrates.

Thus, according to the chromatographic quantitative assay device of embodiment 7, since the chromatographic quantitative assay device is covered with the liquid-impermeable sheet member 7 except both ends thereof, the air-releasing path at infiltration of liquid is restricted to only in the infiltration direction, whereby the liquid sample and marker reagent flow out at uniform concentration.

Embodiment 8

Hereinafter, embodiment 8 of the present invention mentioned in claim 9 will be described.

In this embodiment 8, when the chromatographic quantitative assay device is covered by close adhesion with the liquid-impermeable sheet member 7, an adhesive made of stickiness substance such as acrylic resin is adopted for adhesion of the liquid-impermeable sheet member 7.

Thus, according to the chromatographic quantitative assay device of embodiment 8, since the liquid-impermeable sheet member is closely adhered to the chromatographic quantitative assay device using an arbitrary adhesive, exfoliation of the surface adhered to the sheet member due to the infiltration of the liquid sample does not occur, and consequently, the adhesive strength is increased.

Embodiment 9

Hereinafter, embodiment 9 of the present invention mentioned in claims 10 to 12 will be described.

In this embodiment 9, when the chromatographic quantitative assay device is covered by close adhesion with the liquid-impermeable sheet member 7, an adhesive which hardens after adhesion is adopted for adhesion of the liquid-impermeable sheet member 7.

Thus, according to the chromatographic quantitative assay device of embodiment 9, since the liquid-impermeable sheet member 7 is adhered to the chromatographic quantitative assay device using an adhesive which hardens after adhesion, the adhesive does not infiltrate to the reaction layer carrier after adhesion, whereby the reaction layer is prevented from discoloration or transformation and the specific fixing protein is prevented from transformation or deactivation.

Embodiment 10

Hereinafter, embodiment 10 of the present invention mentioned in claim 13 will be described.

In this embodiment 10, plastic tape as well as other arbitrary liquid-impermeable sheet materials such as vinyl tape, PET (polyethylene terephthalate), are adopted as the material of the liquid-impermeable sheet member 7.

Thus, according to the chromatographic quantitative assay device of embodiment 10, since the liquid-impermeable sheet member 7 comprises a transparent or semi-transparent material, detection by visual observation is possible when measuring the results of the detection region from the outside, whereby the measurement is facilitated.

Embodiment 11

Hereinafter, embodiment 11 of the present invention mentioned in claim 14 will be described.

In this embodiment 11, an arbitrary semi-transparent or opaque liquid-impermeable material is used as a material of the liquid-impermeable sheet member, and a transparent window is provided in the region of the antibody fixing portion 5 (see FIG. 1) as a detection part so as to determine the results of reaction from the outside easily. Further, an arbitrary liquid-impermeable sheet material such a plastic tape, vinyl tape, or PET can be adopted as the material of the window.

Thus, according to the chromatographic quantitative assay device of embodiment 11, a semi-transparent or opaque material is adopted for the liquid-impermeable sheet member, and a transparent window is provided in an arbitrary position of the detection region. Therefore, detection by visual observation is possible when measuring the results of the detection region from the outside, whereby the measurement is facilitated.

Embodiment 12

Hereinafter, embodiment 12 of the present invention mentioned in claims 15 to 18 will be described.

In this embodiment 12, a surfactant, an arbitrary chloride such as sodium chloride and potassium chloride, saponin series, or an arbitrary substance having bacteriolytic effect such as lysozyme is adopted for the cell component destruction substance to be used.

Thus, according to the chromatographic quantitative assay device of embodiment 12, since the sample addition portion holds the above-mentioned cell component destruction substance, even when a liquid sample containing cell components such as whole blood or bacterial solution is added, infiltration is not degraded due to clogging of the cell components and, therefore, it is possible to perform the quantitative assay in short time.

Embodiment 13

Hereinafter, embodiment 13 of the present invention mentioned in claim 19 will be described.

In this embodiment 13, the liquid-impermeable sheet member, which has previously been treated by aging at an arbitrary temperature, is adhered closely to the upper surface and side surfaces of the chromatographic quantitative assay device.

Thus, according to the method of manufacturing the chromatographic quantitative assay device of embodiment 13, since the liquid-impermeable sheet member has previously been treated by aging at an arbitrary temperature, it is possible to facilitate volatilization of organic solvent having a bad influence on the protein and the reaction layer, whereby the preservation stability of the assay device over a longer period of time is realized.

Embodiment 14

Hereinafter, embodiment 14 of the present invention mentioned in claim 20 will be described.

In this embodiment 14, the liquid-impermeable sheet member, which is previously prepared on the chromatographic quantitative assay device, is adhered closely to the upper surface and side surfaces of the chromatographic quantitative assay device by applying an arbitrary pressure to the liquid-impermeable sheet member at an arbitrary temperature.

Thus, according to the manufacturing method of chromatographic quantitative assay device of embodiment 14, since the liquid-impermeable sheet member is adhered closely to the upper surface and side surfaces of the chromatographic quantitative assay device by applying an arbitrary pressure to the liquid-impermeable sheet member at an arbitrary temperature, it is possible to adhere the liquid-impermeable sheet member to the chromatographic quantitative assay device more solidly.

Embodiment 15

Hereinafter, embodiment 15 of the present invention mentioned in claims 21 and 23 will be described.

In this embodiment 15, the liquid-impermeable sheet member 7 is adhered to the chromatographic quantitative assay device, using an adhesive which has characteristics of being melted by heating and taking on stickiness and is hardened after adhesion.

Thus, according to the manufacturing method of chromatographic quantitative assay device of embodiment 15, the liquid-permeable sheet member 7 is adhered to the surface of the chromatographic quantitative assay device, using an adhesive applied to the liquid-impermeable sheet member, which has characteristics of being melted by heating and taking on stickiness and is hardened after adhesion. Therefore, the adhesive does not infiltrate to the chromatographic quantitative assay device during a preservation period, whereby the performance of the chromatographic quantitative assay device can be maintained in stable state over a longer period of time.

EXAMPLES

Next, the present invention will be described more specifically taking some examples. However, those examples described hereinafter are not to restrict the scope of the present invention.

Quantitation of hCG in Urine

An immunochromatographic specimen having an anti-hCG-β antibody fixing line and a broad band of a complex of anti-hCG-α antibody and gold colloid in nitrocellulose membrane, is manufactured. This specimen is shown in FIG. 2. In the figure, the specimen includes an antibody fixing portion 5, a marker reagent holding portion 3 where the complex of anti-hCG-α antibody and gold colloid is contained, which is disposed before the antibody fixing portion 5, and a sample addition portion 2. The way of manufacturing of this specimen is as follows.

Example 1
Preparation of chromatographic specimen:

An anti-hCG-β antibody solution, the concentration of which is adjusted by dilution with phosphoric acid buffer solution, is prepared. This antibody solution is applied onto a nitrocellulose membrane by using a solution discharger. Thereby, antibody fixing line for detection is obtained on the nitrocellulose membrane. After being dehydrated, this nitrocellulose membrane is soaked in Tris-HCl buffer solution containing 1% skim milk, and shaken gently for 30 minutes. After 30 minutes has passed, the membrane is moved to a Tris-HCl buffer solution bath and shaken gently for 10 minutes and, thereafter, it is moved to another Tris-HCl buffer solution bath and shaken gently for more 10 minutes, whereby the nitrocellulose membrane is washed. After being washed twice, the membrane is taken out of the washing solution, and dehydrated at room temperature.

Gold colloid is prepared in such a way that 1% citric acid solution is added to 0.01% gold chloride acid solution at 100° C. while circulating. After circulation for 30 minutes, the solution is cooled. Anti-hCG-α antibody is added to the gold colloidal solution which is prepared in pH 9 by 0.2M potassium carbonate solution and then the gold colloidal solution is stirred for several minutes and, thereafter, 10% BSA (bovine serum albumin) solution of pH 9 is added by such amount that the final concentration thereof will be 1% and then the gold colloidal solution is stirred, whereby antibody gold colloidal complex (marker antibody) is prepared. Then, this marker antibody solution is subjected to centrifugation for 50 minutes at 4° C. by 20000G to separate a marker antibody as a simple, and the marker antibody is suspended in washing buffer solution (1% BSA, phosphoric acid buffer solution), followed by centrifugation, whereby the marker antibody is washed and separated as a simple. This marker antibody is suspended in washing buffer solution and then filtrated with a 0.8 μm filter and, thereafter, the marker antibody is prepared to be ⅒ of the original gold colloidal solution and then stored at 4° C.

The marker antibody solution is set in a solution discharger, and applied onto a part of the anti-hCG-β antibody fixing dehydrated membrane, which part is away from the position where the antibody is fixed, and thereafter, the membrane is dehydrated. Thereby, the marker antibody holding portion is made on the fixed membrane.

The antibody fixing membrane including the marker antibody holding portion, which is prepared as mentioned above, is stuck onto the reaction layer carrier support, and non-woven fabric and glassfiber filter are added as a sample addition portion and a absorption portion, respectively. Thereafter, the membrane is cut into strips of 0.5 cm width, and a transparent tape is stuck over the upper surface of each strip except the half of the sample addition portion, whereby a specimen is fabricated.

Example 2
Preparation of sample:

By adding hCG solutions of already-known concentrations into male urine of human, hCG solutions of various already-known concentrations are prepared.

Example 3
Measurement of coloration degree:

The male urine of human containing respectively 0 U/l, 100 U/l, 1000 U/l and 10000 U/l of hCG, are added to specimens, and then developed. Thereafter, the state of coloration, to the male urine of human of each concentration of hCG, at the antibody fixing portion on the specimens is measured with a reflecting spectrophotometer. Absorbance at 520 nm wavelength is measured, and is substituted for a previously-formed calibration curb which shows the relationship between the concentration of hCG and the absorbance. The result is shown in FIG. 7. Primarily, when absorbance of male urine of human containing 1000 U/l hCG is measured and substituted for the calibration curb, the hCG concentration ought to be 1000 U/l. In practice, however, there is a slight divergence, and by the degree of that divergence, accuracy of the measurement can be known.

Figure 7A:
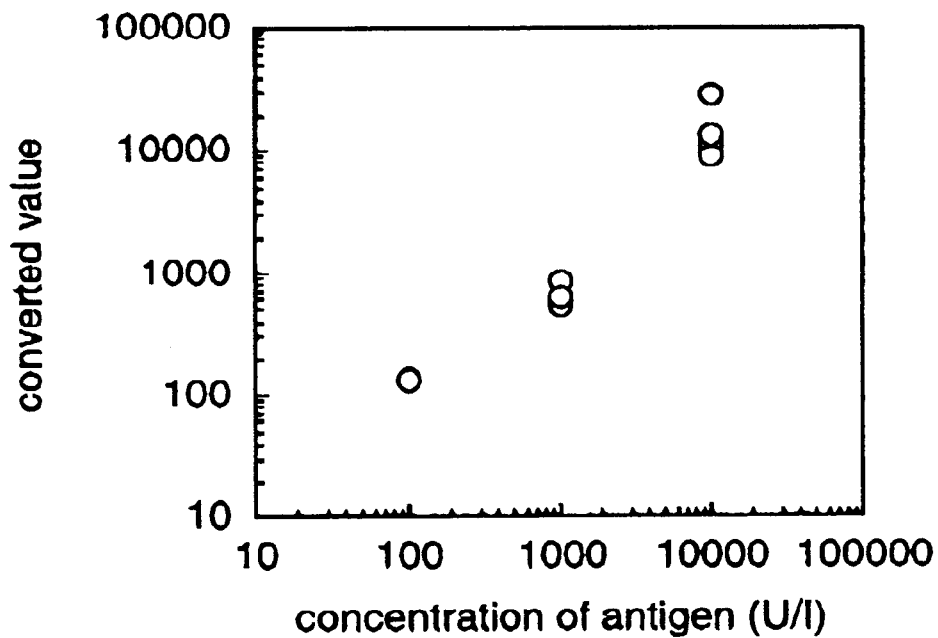
FIG. 7 is a graphic chart, as an experimental example, which shows the quantitative performance of a reaction layer carrier in case of being covered with a liquid-impermeable sheet member (A) and in case without a liquid-impermeable sheet member (B).
Figure 7B:
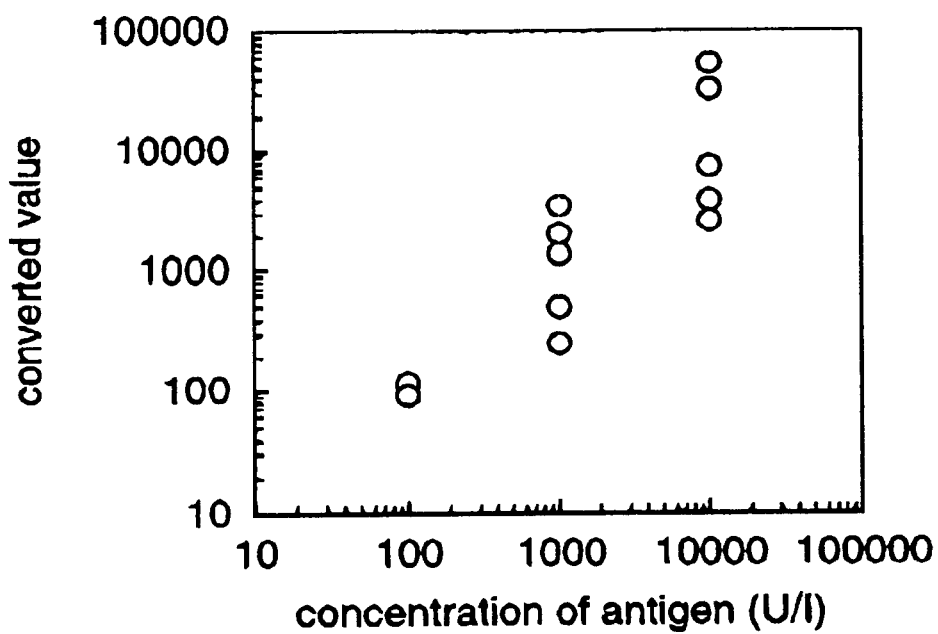

FIG. 7(a) is a diagram showing the quantitative performance of a chromatographic quantitative assay device covered with a liquid-impermeable sheet member, and FIG. 7(b) shows the quantitative performance of a chromatographic quantitative assay device having no liquid-impermeable sheet member.

In FIG. 7, converted results of the concentrations of the analyte are shown on the basis of the measured values of coloration at a point of 3 minutes after addition of a liquid sample to the chromatographic quantitative assay device. In the case with the sheet member (FIG. 7(a)), CV values (coefficients of variation) are within the range from 0 to 10%. On other hand, in the case without the sheet member, CV values (FIG. 7(b)) vary from 27 to 42%, and this large dispersion indicates that the quantitative performance is inferior. From this result, it is understood that covering a chromatographic quantitative assay device with a liquid-impermeable sheet member is greatly concerned with the improvement of quantitative performance.

In the chromatographic quantitative assay device according to the embodiments of the present invention, the specimen comprising a chromatographic material composed of an arbitrary porous carrier, such as nitrocellulose or glassfiber filter, is used. The specimen made of the materials of this kind has a function to analyze, detect, and determine a specific substance by utilizing an arbitrary principle of measurement such as antigen-antibody reaction. Furthermore, the liquid sample to be measured includes water, water solution, urine, blood, body fluid, any solution wherein solid and powder or gas is dissolved, and the purpose of use includes urinalysis, gestation test, water analysis, excreta analysis, soil analysis, food composition analysis, or the like.

By the above-mentioned constitution, an analyte which exists in a liquid sample as an arbitrary solution to be analyzed can be subjected to simple and reliable quantitative assay in short time.

APPLICABILITY IN INDUSTRY

According to the chromatographic quantitative assay device and the manufacturing method thereof according to the present invention, when liquid sample is added on a specimen and measurement started, vaporization of the liquid sample is prevented, and the air-releasing path at infiltration of liquid is restricted in only the infiltration direction, whereby infiltration of the liquid sample is made uniform. In other words, it is possible to make the liquid sample and marker reagent, which flow out in a constant time, flow out at uniform concentration. Further, since the affection of background values added on the color-reacted portions is reduced, it is possible to perform the assay in short time, resulting in a chromatographic quantitative assay device with higher sensitivity and higher performance.

What is claimed is:

1. A chromatographic quantitative assay device comprising:
    a non-moistenable reaction layer carrier support, and a moistenable layer which is formed above the support and consists of a material or an arbitrary number of materials;
    said moistenable layer comprising a portion for adding a liquid sample, a portion for holding a migratable marker reagent, a portion that performs binding reaction with a marker reagent which is provided with a substance capable of being bound specifically to an analyte in the liquid sample, and a portion for absorbing the liquid sample; and
    a liquid-impermeable sheet member which is provided being adhered to the upper surface and side surfaces except the portion for adding a liquid sample.

2. A chromatographic quantitative assay device comprising:
    a non-moistenable reaction layer carrier support, and a moistenable layer which is formed above the support and consists of a material or an arbitrary number of materials;
    said moistenable layer comprising a portion for adding a liquid sample, a portion for holding a predetermined quantity of migratable combined reagent which is previously prepared consisting of an analyte and a marker reagent, a portion that performs competitive binding reaction between an analyte in the liquid sample and the combined reagent provided with a substance capable of being bound specifically to the analyte in the liquid sample, and a portion for absorbing the liquid sample; and
    a liquid-impermeable sheet member which is provided being adhered to the upper surface and side surfaces except the portion for adding a liquid sample.

3. A chromatographic quantitative assay device comprising:
    a non-moistenable reaction layer carrier support, and a moistenable layer which is formed above the support and consists of a material or an arbitrary number of materials;
    said moistenable layer comprising a portion for adding a liquid sample where a substance for destroying cell components in the liquid sample is held, a portion for holding a migratable marker reagent, a portion that performs binding reaction with the marker reagent provided with a substance capable of being bound specifically to an analyte in the liquid sample, and a portion for absorbing the liquid sample; and
    a liquid-impermeable sheet member which is provided being adhered to the upper surface and side surfaces except the portion for adding a liquid sample.

4. A chromatographic quantitative assay device comprising:
    a non-moistenable reaction layer carrier support, and a moistenable layer which is formed above the support and consists of a material or an arbitrary number of materials;
    said moistenable layer comprising a portion for adding a liquid sample where a substance for destroying cell components in the liquid sample is held, a portion for holding a constant quantity of migratable combined reagent which is previously prepared consisting of an analyte and a marker reagent, a portion that performs competitive binding reaction between an analyte in the liquid sample and the combined reagent provided with a substance capable of being bound specifically to the analyte in the liquid sample, and a portion for absorbing the liquid sample; and
    a liquid-impermeable sheet member which is provided being adhered to the upper surface and side surfaces except the portion for adding a liquid sample.

5. A chromatographic quantitative assay device as defined in any of claims 1 to 4, wherein the liquid-impermeable sheet member is provided on the upper surface, or from the upper surface to the back surface, except the portion for adding a liquid sample.

6. A chromatographic quantitative assay device as defined in any of claims 1 to 4, wherein the vertical side surfaces of the liquid-impermeable sheet member is opened in the direction where the liquid sample infiltrates.

7. A chromatographic quantitative assay device as defined in any of claims 1 to 4, wherein the end of the liquid-impermeable sheet member is opened at an arbitrary position at the end of the chromatographic quantitative assay device in the direction where the liquid sample infiltrates.

8. A chromatographic quantitative assay device as defined in any of claims 1 to 4, wherein the liquid-impermeable sheet member is adhered by an arbitrary adhesive which hardens after adhesion.

9. A chromatographic quantitative assay device as defined in any of claims 1 to 4, wherein the liquid-impermeable sheet member is adhered by an adhesive made of an arbitrary adhesive.

10. A chromatographic quantitative assay device as defined in claim 9, wherein the adhesive applied to the liquid-impermeable sheet member is made of thermoplastic resin.

11. A chromatographic quantitative assay device as defined in claim 9, wherein the adhesive applied to the liquid-impermeable sheet member is made of thermosetting resin.

12. A chromatographic quantitative assay device as defined in any of claims 1 to 4, wherein the liquid-impermeable sheet member is made of an arbitrary transparent or semi-transparent liquid-impermeable material.

13. A chromatographic quantitative assay device as defined in any of claims 1 to 4, wherein the liquid-impermeable sheet member is made of an arbitrary semi-transparent or opaque liquid-impermeable material, and a transparent window is provided at the detection region.

14. A chromatographic quantitative assay device as defined in claim 3 or claim 4, wherein the substance for destroying cell components held at the portion for adding a liquid sample is a surfactant.

15. A chromatographic quantitative assay device as defined in claim 3 or claim 4, wherein the substance for destroying cell components held at the portion for adding a liquid sample is composed of chloride.

16. A chromatographic quantitative assay device as defined in claim 3 or claim 4, wherein the substance for destroying cell components held at the portion for adding a liquid sample is saponin series.

17. A chromatographic quantitative assay device as defined in claim 3 or claim 4, wherein the substance for destroying cell components held at the portion for adding a liquid sample is a substance having bacteriolytic effect.

18. A chromatographic quantitative assay device as defined in claim 3 or claim 4, wherein the substance for destroying cell components held at the portion for adding a liquid sample is composed of sodium chloride.

19. A chromatographic quantitative assay device as defined in claim 3 or claim 4, wherein the substance for destroying cell components held at the portion for adding a liquid sample is composed of potassium chloride.

20. A chromatographic quantitative assay device as defined in claim 3 or claim 4, wherein the substance for destroying cell components held at the portion for adding a liquid sample is lysozyme.

21. A method of manufacturing a chromatographic quantitative assay device as defined in any of claims 1 to 4, wherein the liquid-impermeable sheet member is adhered closely to the upper surface and side surfaces of the chromatographic quantitative assay device by applying of an arbitrary pressure to the liquid-impermeable sheet member at an arbitrary temperature.

22. A method of manufacturing a chromatographic quantitative assay device as defined in any of claims 1 to 4, wherein the liquid-impermeable sheet member, which is previously treated by performing aging at an arbitrary temperature, is adhered closely to the upper surface and side surfaces of the chromatographic quantitative assay device.

23. A method of manufacturing a chromatographic quantitative assay device as defined in claim 22, wherein the adhesive applied to the liquid-impermeable sheet member has a characteristic of being melted and taking on stickiness at the temperature higher than room temperature and is hardened after adhesion.

24. A method of manufacturing a chromatographic quantitative assay device as defined in claim 23, wherein the adhesive applied to the liquid-impermeable sheet member is made of thermoplastic resin.

25. A manufacturing method of a chromatographic quantitative assay device as defined in claim 23, wherein the adhesive applied to the liquid-impermeable sheet member is made of thermosetting resin.

26. A method of manufacturing a chromatographic quantitative assay device as defined in claim 21, wherein the adhesive applied to the liquid-impermeable sheet member has a characteristic of being melted and taking on stickiness at the temperature higher than room temperature and is hardened after adhesion.

27. A method of manufacturing a chromatographic quantitative assay device as defined in claim 26, wherein the adhesive applied to the liquid-impermeable sheet member is made of thermoplastic resin.

28. A manufacturing method of a chromatographic quantitative assay device as defined in claim 26, wherein the adhesive applied to the liquid-impermeable sheet member is made of thermosetting resin.

29. A chromatographic quantitative assay device comprising:
  a moistenable layer consisting of a material or an arbitrary number of materials;
  said moistenable layer comprising
    a portion for adding a liquid sample,
    a portion for holding a migratable marker reagent,
    a portion that performs binding reaction with a marker reagent which is provided with a substance capable of being bound specifically to an analyte in the liquid sample, and
    a portion for absorbing the liquid sample; and
  a liquid-impermeable sheet provided on the periphery of the device except the portion for adding a liquid sample.

* * * * *